(12) United States Patent
Franco et al.

(10) Patent No.: US 11,730,824 B2
(45) Date of Patent: *Aug. 22, 2023

(54) DRUG-RELEASING COMPOSITIONS OF METAL OXIDE SEMICONDUCTOR NANOMATERIALS AND HEMOSTATIC POLYMERS

(71) Applicant: NSC NANO SONO COOPERATION LTD., Yokneam Illit (IL)

(72) Inventors: Ariel Antonio Franco, Yokneam Illit (IL); Rajashekharayya A. Sanguramath, Yokneam Illit (IL)

(73) Assignee: NSC NANO SONO COOPERATION LTD., Yokneam Illit (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/246,732

(22) Filed: May 3, 2021

(65) Prior Publication Data

US 2021/0322566 A1 Oct. 21, 2021

Related U.S. Application Data

(63) Continuation-in-part of application No. 16/892,493, filed on Jun. 4, 2020, now Pat. No. 10,998,467, and
(Continued)

(51) Int. Cl.
*A61K 47/69* (2017.01)
*A61K 31/245* (2006.01)
(Continued)

(52) U.S. Cl.
CPC ........ *A61K 47/6929* (2017.08); *A61K 31/192* (2013.01); *A61K 31/245* (2013.01); *A61K 47/61* (2017.08)

(58) Field of Classification Search
CPC .............. A61K 47/6929; A61K 31/192; A61K 31/245; A61K 47/61; A61K 47/6923;
(Continued)

(56) References Cited

U.S. PATENT DOCUMENTS 8,425,880 B1 4/2013 Lyczak et al.
10,998,467 B2 * 5/2021 Franco .................. A01N 59/16
(Continued)

FOREIGN PATENT DOCUMENTS

WO 2002039963 5/2002
WO 2003080231 10/2003
(Continued)

OTHER PUBLICATIONS

Gao, et al., A polymer-based systemic hemostatic agent, Sci. Adv. 2020; 6(31): eaba0588, pp. 1-12 (Year: 2020).*
(Continued)

*Primary Examiner* — Daniel C. McCracken
(74) *Attorney, Agent, or Firm* — JMB Davis Ben-David

(57) ABSTRACT

The present disclosure generally relates to metal oxide semiconductor nanomaterial compositions that include hemostatic polymers and pharmaceutical agents. Methods of producing the noted nanomaterials, and of their use in therapeutic applications are also described.

17 Claims, 10 Drawing Sheets

Related U.S. Application Data a continuation-in-part of application No. 16/582,529, filed on Sep. 25, 2019, now Pat. No. 10,995,011.

(60) Provisional application No. 62/793,445, filed on Jan. 17, 2019.

(51) Int. Cl.
*A61K 31/192* (2006.01)
*A61K 47/61* (2017.01)

(58) Field of Classification Search
CPC .......... A01N 25/34; A01N 59/20; C01G 9/00; C01G 9/02; C01G 3/02; C01P 2002/72; C01P 2002/82; C01P 2004/04; C01P 2004/64; C01P 2004/82; C01P 2004/88; C01P 2006/12
See application file for complete search history.

(56) References Cited

U.S. PATENT DOCUMENTS

| | | |
|---|---|---|
| 2007/0275101 A1 | 11/2007 | Lu |
| 2008/0085326 A1 | 4/2008 | Hai |
| 2008/0317830 A1 | 12/2008 | Goldstein |
| 2013/0168328 A1 | 7/2013 | Bagabas |
| 2013/0315972 A1 | 11/2013 | Krasnow |
| 2014/0017462 A1 | 1/2014 | Nicholas |
| 2014/0276322 A1 | 9/2014 | Murphy |
| 2015/0196066 A1 | 7/2015 | Bert |
| 2016/0250612 A1 | 9/2016 | Oldenberg |
| 2017/0252440 A1 | 9/2017 | Wu |
| 2018/0036426 A1 | 2/2018 | Rajh |
| 2020/0100503 A1 | 4/2020 | Kanovsky |

FOREIGN PATENT DOCUMENTS

| | | |
|---|---|---|
| WO | 2004101014 | 11/2004 |
| WO | 2006048879 | 5/2006 |
| WO | 2007147842 | 12/2007 |
| WO | 2018099945 | 6/2018 |
| WO | 2020041472 | 2/2020 |

OTHER PUBLICATIONS

Diez-Pascual, et al., Wound Healing Bionanocomposites Based on Castor Oil Polymeric Films Reinforced with Chitosan-Modified ZnO Nanoparticles, Biomacromolecules 2015; 16: 2631-2644 (Year: 2015).*

Arshad, et al., Zn-doped SiO2 nanopartides preparation and characterization under the effect of various solvents: Antimicrobial, antifungal and photocatlytic performance evaluation, Journal of Photochemistry & Photobiology, B: Biology 2018; 185: 176-183.

Assal, et al.; "Synthesis, Characterization, and Relative Study on the Catalystic Activity of Zinc Oxide Nanoparticles doped MnCO3, MnO2, Mn2O3 for Ariel Oxidation of Alcohols", Journal of chemistry, 2017 (Jul. 12, 2017).

Brady, et al., Mineral Formulae Recalculation, accessed online at https://serc.carleton.edu/research_education/equilibria/mineralformulaerecalculation.html on Dec. 22, 2020.

Carbone, et al. "Antimicrobial power of Cu/Zn mixed oxide nanopartides to *Escherichia coli*." Environmental Nanotechnology, Monitoring & Management 7 (May 1, 2017): 97-102.

Carbone, et al., Antimicrobial power of Cu/Zn mixed oxide nanopartides to *Escherichia coli*, Environmental Nanotechnology, Monitoring & Management 2017; 7: 97-102.

International Search Report of PCT/US20/13793, dated Mar. 19, 2020.

Kozhushner, et al. "Inhomogeneous charge distribution in semiconductor nanoparticles." The Journal of Physical Chemistry C 119.28 (Jul. 16, 2015): 16286-16292.

Lin, et al. "Band gap variation of size-controlled ZnO quantum dots synthesized by sol-gel method." Chemical Physics Letters 409.4-6 (Jun. 30, 2005): 208-211.

Periodic Table Atomic Properties of the Elemetns, NIST SP 966 (Sep. 2010).

Tamanis, et al., "Synthesis of Core/Shell CuO—Zno Nanopartides and Their Second-Harmonic Generation performance" Latvian Journal of Physics and Technical Sciences 52.5 (Oct. 1, 2015): 41-46.

Tamanis, et al., Synthesis of Core/Shell CuO—ZnO Nanopartides and Their Second-Harmonic Generation performance, Latvian Journal of Physics and Technical Sciences 2015; 5:41-16.

Tenorite, accessed online at http://www.handbookofmineralogy.com/pdfs/tenorite.pdf (2005).

Vaseem, et al. "Copper oxide quantum dot ink for inkjet-driven digitally controlled high mobility field effect transistors." Journal of Materials Chemistry C 1.11 (Jan. 24, 2013): 2112-2120.

Wang, et al. "Reduced graphene oxide decorated with CuO—ZnO hetero-junctions: towards high selective gas-tensing property to acetone." Journal of Materials Chemistry A 2.43 (Sep. 19, 2014): 18635-18643.

Wang, et al., Reduced graphene oxide decorated with CuO—ZnO hetero-junctions: towards high selective gas-tensing property to acetone, J. Mater. Chem. A 2014; 2:18635-18643.

Zatsepin, et al., Electronic structure and photoluminescence properties of Zn-ion implanted silica glass before and after thermal annealing. Journal of Non-Crystalline Solids 2016; 423: 183-188.

\* cited by examiner

DRUG-RELEASING COMPOSITIONS OF METAL OXIDE SEMICONDUCTOR NANOMATERIALS AND HEMOSTATIC POLYMERS

CROSS REFERENCE TO RELATED APPLICATIONS

This is a continuation-in-part of U.S. patent application Ser. No. 16/582,529, filed Sep. 25, 2019, which claims priority to U.S. Provisional Patent Application No. 62/793,445, filed Jan. 17, 2019. This is also a continuation-in-part of U.S. patent application Ser. No. 16/892,493, filed Jun. 4, 2020. The contents of the foregoing patent applications are incorporated by referenced herein in their entirety.

FIELD

The present disclosure generally relates to metal oxide semiconductor nanomaterial compositions that include hemostatic polymers and pharmaceutical agents. Methods of producing the noted nanomaterials, and of their use in therapeutic applications are also described.

BACKGROUND

Integrity of the skin is generally compromised in traumatic or surgical events Immediately after the injury, first-aid is administered to manage blood loss, pain, and microbial infection around the affected area. Wound dressings that include active materials to reduce blood loss (hemostatic), quickly reduce or eliminate pain, and control infection are essential for initiating and advancing normal healing. Currently, there are no practical wound dressings in the market which comprehensively address these key issues.

Metal oxide semiconductor nanomaterials and especially copper oxide (CuO) and zinc oxide (ZnO) nanomaterials ($CuO_{(1-x)}ZnO_x$) have been shown to possess antibacterial, antimicrobial, and antifungal properties (see US Patent Publication No. 2020/0231459). Compositions that include such metal-oxide nanomaterials that are coated by a hemostatic polymer were also recently described (see US Patent Publication No. 2021/0091266).

However, a continuing need exists for nanomaterials that can be applied to wound dressings and which are antimicrobial, hemostatic, and which also provide pharmaceutical benefits such as analgesia.

SUMMARY

Provided herein is a metal oxide semiconductor nanocomposite composition, that includes a metal oxide nanomaterial consisting of a CuO and ZnO nanomaterial consisting of clusters of CuO and ZnO quantum dots, wherein the nanomaterial has a chemical formula of $CuO_{(1-x)}ZnO_x$, wherein X is the atomic ratio of zinc oxide impurities in the nanomaterial; a hemostasis-promoting polymer coating the metal oxide nanomaterial in which the polymer can be in particular embodiments chitosan and derivatives thereof, calcium salt of alginate and divalent cation alginate derivatives thereof, polylysine, or oxidized cellulose; and a pharmaceutically active drug conjugated to the hemostasis-promoting polymer.

In particular embodiments, the metal oxide nanomaterial has a surface region and a core region, wherein the surface region is greater than 25% ZnO by weight and less than 75% CuO by weight, and wherein the core region is less than 10% ZnO by weight and greater than 90% CuO by weight.

In some embodiments, the hemostasis-promoting polymer is from 1% to about 10% of the metal oxide semiconductor nanocomposite by weight. In other embodiments, the thickness of the hemostasis-promoting polymer coating is from about 1.0 nm to about 10.0 nm.

In certain embodiments, the hemostasis-promoting polymer is selected from chitosan, alginate, gelatin, carboxymethyl cellulose, and polyethylene glycol.

In particular embodiments, the pharmaceutically active drug conjugated to the hemostasis-promoting polymer is a small molecule pharmaceutical agent or a biological entity, such as a polynucleotide, polypeptide, or antibody.

In other particular embodiments, the pharmaceutically-active drug conjugated to the polymer is selected from an analgesic, opioid, local anesthetic, and non-steroidal anti-inflammatory drug (NSAID). In still further particular embodiments, the pharmaceutically-active drug is an analgesic and/or anti-inflammatory drug selected from tetracaine, tetracaine hydrochloride, procaine, procaine hydrochloride, ibuprofen, lidocaine, diclofenac, acetaminophen, and aspirin.

In some embodiments, the pharmaceutically-active drug is conjugated to the polymer by covalent interactions. In other embodiments it is conjugated to the polymer by non-covalent interactions.

In particular embodiments, the metal oxide semiconductor nanocomposite composition is a component of a pharmaceutical composition that also includes a pharmaceutically acceptable salt, carrier, or excipient.

Also provided herein is method for treating a wound by contacting a wound with the described metal oxide semiconductor nanocomposite composition or nanocomposite-containing pharmaceutical composition, wherein the drug is released to the site of contact.

In particular embodiments of the described methods, the drug is released as a burst or gradually over an extended period in response to changes in local pH, temperature changes, hydrolysis, an enzyme-catalyzed release, or combinations thereof.

In some embodiments the administered composition is antimicrobial, hemostatic, anesthetic, anti-inflammatory, or a combination thereof.

In still other embodiments, the composition is formulated for administration by first-aid gauze, wound dressing foams and films, topical ointment, or topical spray.

Additionally provided herein, is a method for inhibiting microbial growth in a subject by administering to a subject in need thereof the described metal oxide semiconductor nanocomposite composition, wherein the microbe is bacteria, fungi, or a virus. In some embodiments of the described methods, the metal oxide semiconductor nanocomposite composition is formulated for topical administration by first-aid gauze, wound dressing foams and films, topical ointment, or topical spray.

Further provided herein is a method for producing a metal oxide semiconductor nanocomposite composition that includes a drug-conjugated polymeric layer, wherein the method proceeds according to the following steps: providing a metal oxide nanocomposite composition; solubilizing a polymer selected from the group consisting of chitosan, alginate, gelatin, carboxymethyl cellulose, and polyethylene glycol; conjugating a pharmaceutical drug to the polymer, thereby producing a polymer-drug conjugate; and coating the metal oxide nanocomposite composition with the polymer-drug conjugate, wherein drug loading efficiency to the polymer-drug conjugate is from 10% to about 90%.

The foregoing and other objects, features, and advantages will become more apparent from the following detailed description, which proceeds with reference to the accompanying figures.

DETAILED DESCRIPTION

I. Terms

Figure 1:
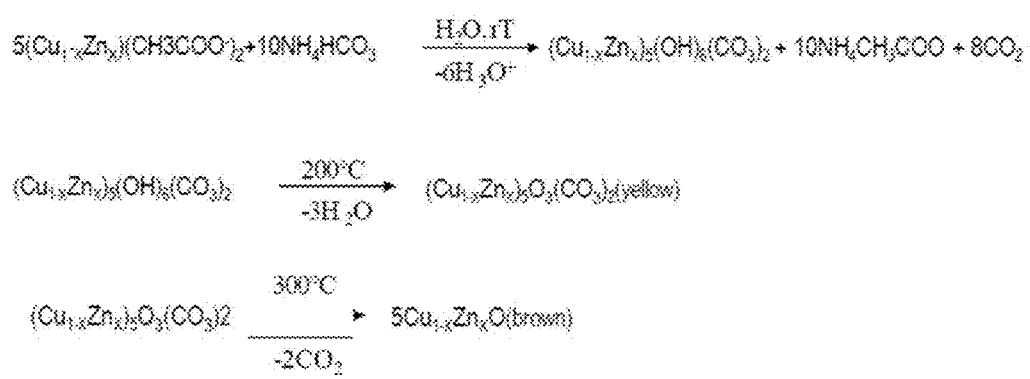
FIG. 1 is a chemical scheme for the nanoparticle preparation. The scheme demonstrates preparation and precipitation of amorphous precursor in the first step; the dehydration of the amorphous precursor in step 2; and thermal decomposition of the Aurichalcite precursor to metal oxide to form the metal oxide semiconductor nanomaterials in step 3.
Figure 2:
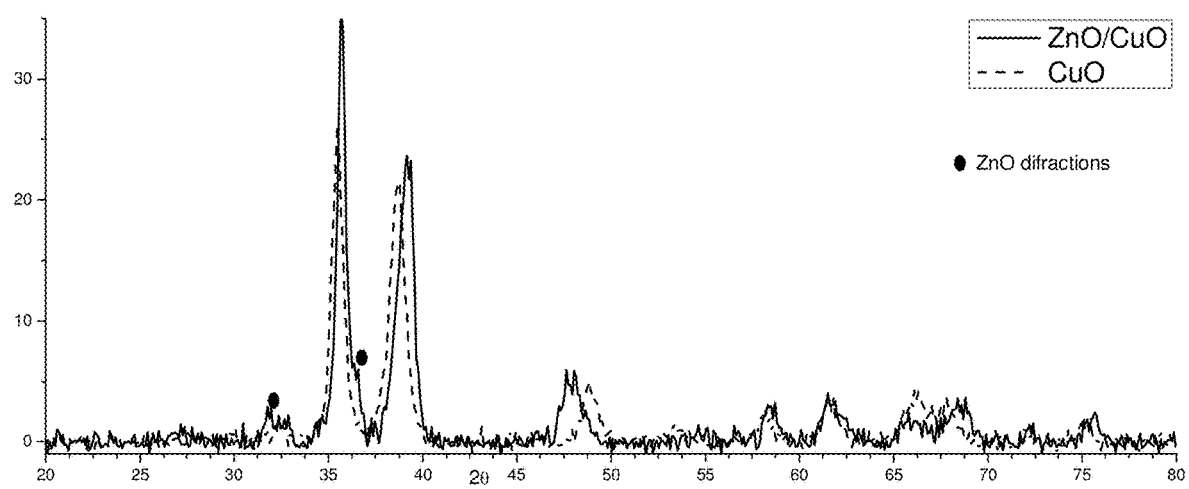
FIG. 2 is a comparison of the XRD diffractograms for pure CuO and $CuO_{(1-x)}ZnO_x$. The diffractograms show the shift for some diffraction signals related to ZnO faces.
Figure 3:
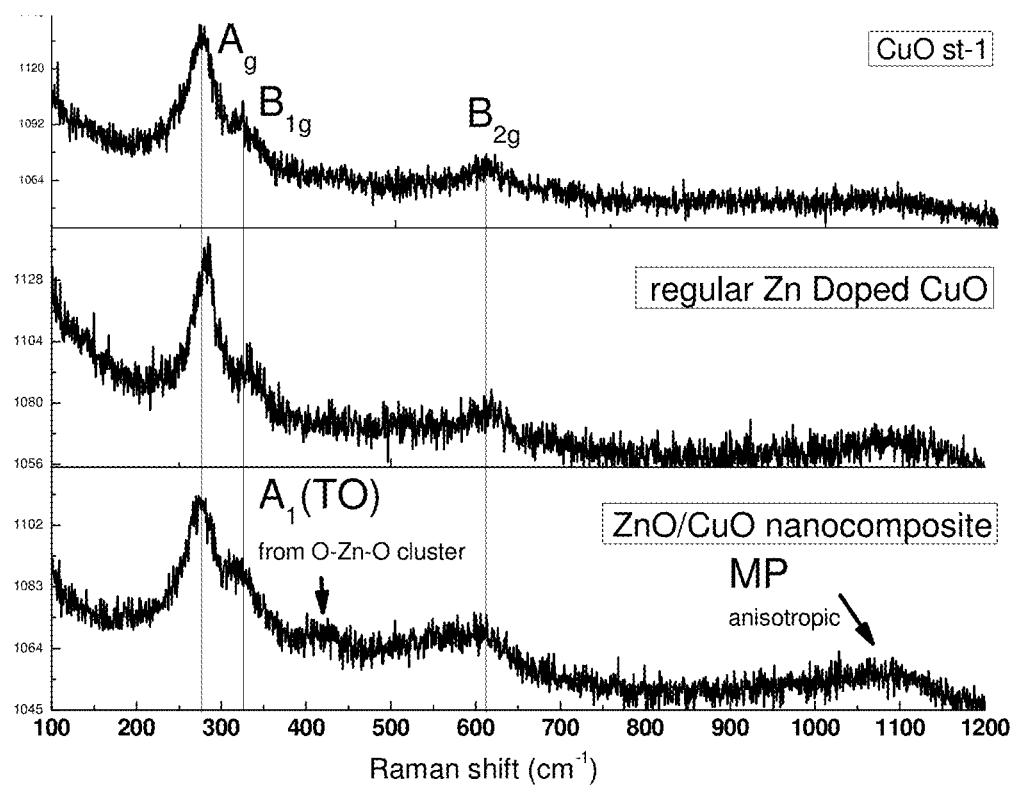
FIG. 3 is a comparison of Raman spectra for pure CuO, regular Zn doped CuO, and $CuO_{(1-x)}ZnO_x$. From this comparison, the loss of symmetry on the whole structure (broad signals), new peaks related with the presence of O—Zn—O clusters, and probable presence of heterojunction due to the increment of multiphoton mode MP that is evidence of anisotropic conduction of electrons is shown.
Figure 4:
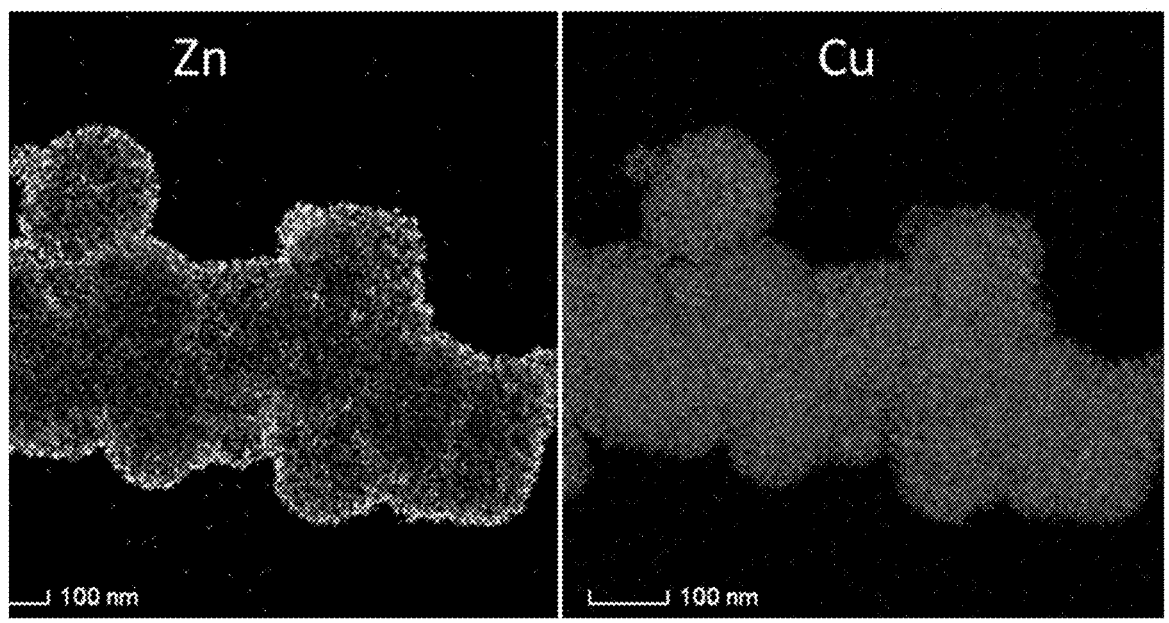
FIG. 4 is a High-resolution transmission electron microscopy (HR-TEM) with EDS detection for Zn (left panel) and Cu (right panel) which shows a non-homogenous distribution of those components and a clear core/shell structure. 100 nm scale bar is shown in both panels.
Figure 5:
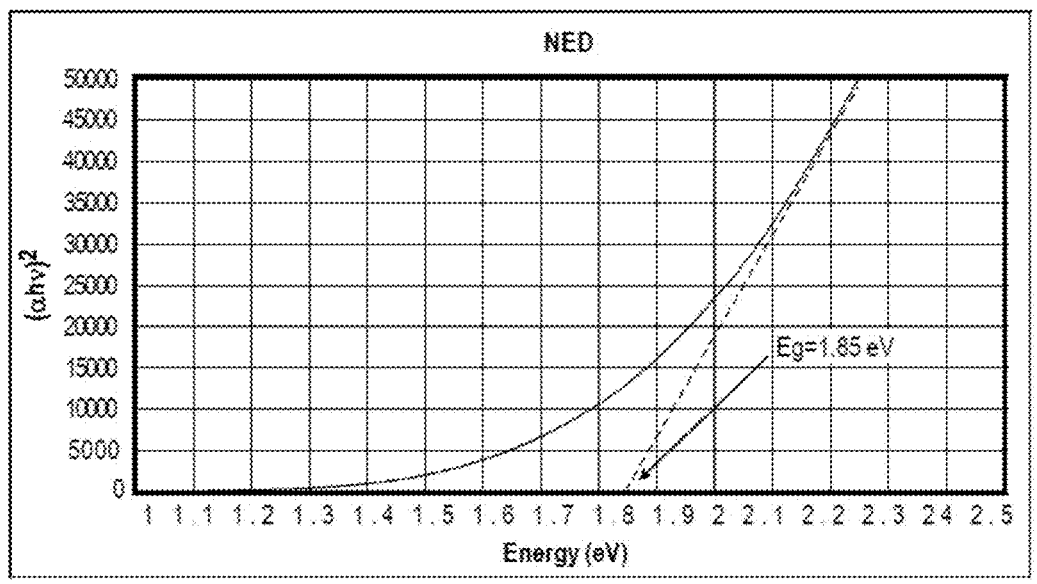
FIG. 5 shows the optical band gap Eg calculation from the UV-vis spectrum of the metal oxide nanomaterials.
Figure 6:
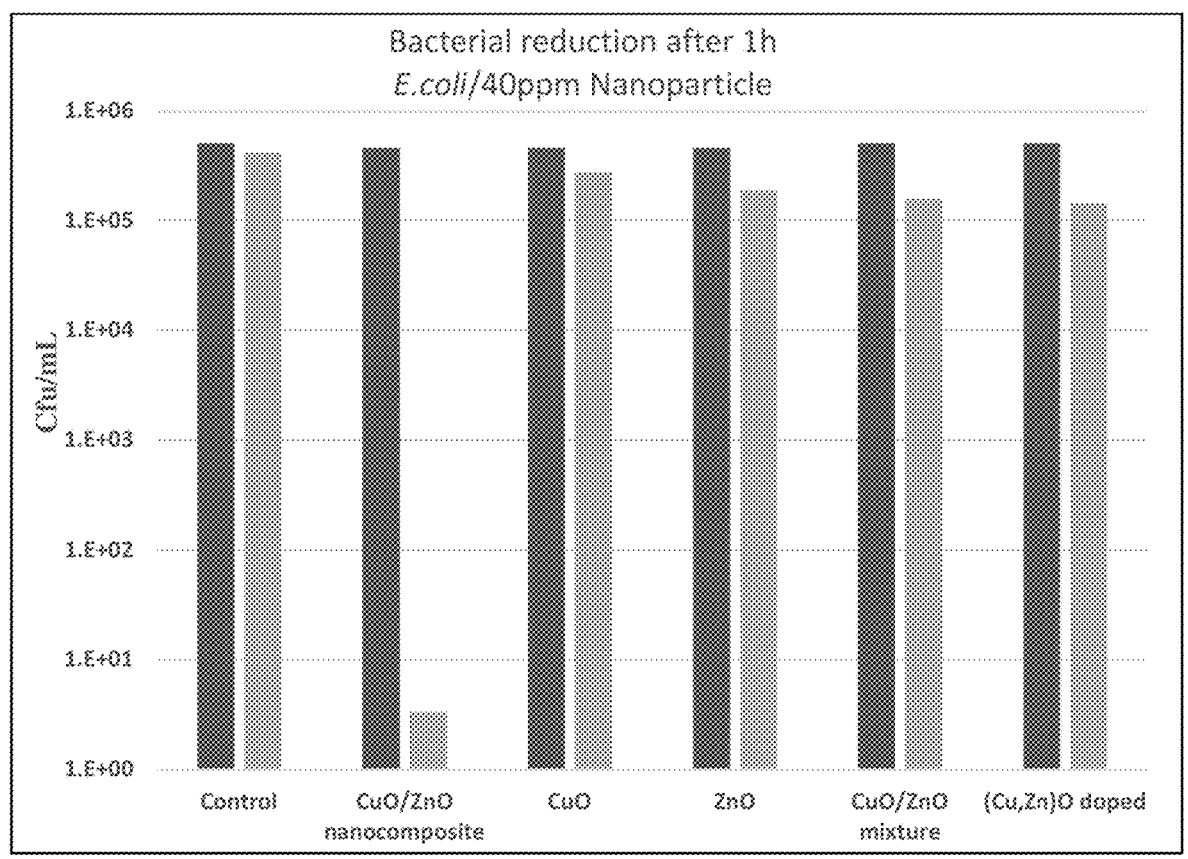
FIG. 6 is a representation showing the bactericidal activity against *E. coli* in saline and 5% fetal bovine serum (FBS) to simulate the wound fluid conditions according to ISO requirement. In both cases, within one hour of exposure, a total elimination of the *E. coli* in saline and 5% fetal bovine serum (FBS) was seen.
Figure 7:
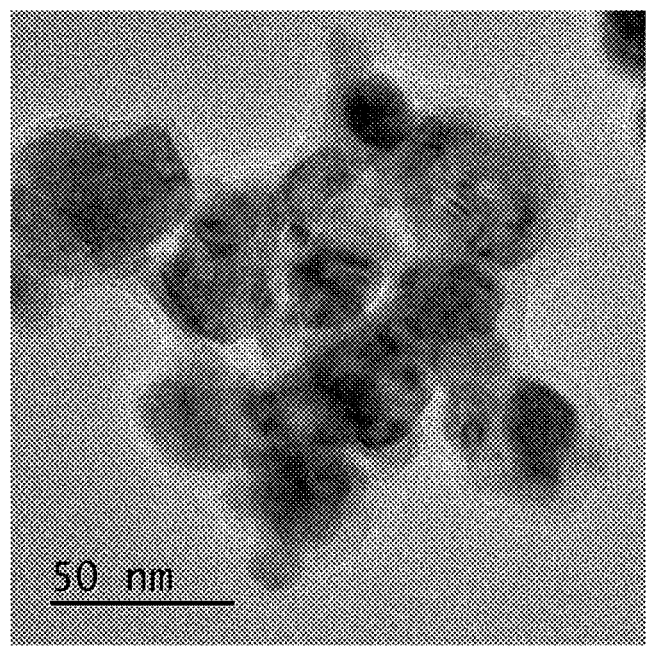
FIG. 7 shows a TEM image of a hemostatic polymer coated on the $CuO_{(1-x)}ZnO_x$.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all molecular weight or molecular mass values are approximate, and are provided for illustrative description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into or onto a subject by a chosen route. For example, the described polymer-nanoparticle composite compounds can be administered locally at a wound site by any method known to the art of contacting a surface with a compound.

Antimicrobial agent: A compound that inhibits, prevents, or eradicates the growth, replication, spread or activity of a microorganism. In a particular embodiment, an antimicrobial agent is a metal oxide nanoparticle component of the described polymer-nanoparticle composite compounds. When used generally, an antimicrobial agent can inhibit, prevent, or eradicate the growth and spread of living microbes such as bacteria and fungi. Similarly, an antimicrobial agent can also inhibit the viability of a viral particle to infect and successfully replicate within a host, thereby eradicating its presence from the host. A microbe may be inhibited when its presence or activity is decreased by at least 10%, at least 20%, at least 30%, at least 50%, at least 80%, at least 100% or at least 250% or more as compared to a microbe that has not been contacted with the compound.

Contacting: Placement in direct physical association; including contact of a surface by a composition both in solid and liquid forms. Contacting can occur in vivo by administering to a subject.

Composite: A material composed of two or more constituent parts, which are generally structurally and physically distinct. A nanocomposite material is of a size in the nanometer (nm) range, typically 1 to 1000 nm Effective amount of a compound: A quantity of compound sufficient to achieve a desired effect. In a therapeutic context, a therapeutically effective amount of a compound is that amount to achieve a desired effect in a subject being treated. For example, the therapeutically effective amount of the described polymer-nanoparticle composite compound in a solid matrix (such as a bandage) will be the amount necessary to enhance/assist hemostasis and provide antimicrobial effects when brought into contact with a wound.

Hemostasis-promoting polymer: A polymer known in the art to possess hemostasis-promoting properties. One example of a hemostasis-promoting is calcium alginate.

Nanoparticle: A particle with a diameter in the nanometer (nm) range, typically 1 to 1000 nm.

Non-covalent bond: A bond formed between two oppositely charged compounds, but does not involve sharing of one or more electrons between atoms, in contrast with a covalent bond which requires electron sharing between atoms.

Pharmaceutical agent: A chemical compound or composition capable of inducing a desired therapeutic or prophylactic effect when properly administered to a subject. Pharmaceutical agents include small molecule compounds as well as biomolecules such as polynucleotides and polypeptides.

Pharmaceutically acceptable carriers, salts, excipients: The pharmaceutically acceptable carriers, salts, and excipients useful in this disclosure are conventional. *The Science*

*and Practice of Pharmacy*, Adeboye Adejare, Ed., 23rd Edition (2020), describes compositions and formulations suitable for pharmaceutical delivery of the compounds herein disclosed. In general, the nature of the carrier, salt, and excipient will depend on the particular mode of administration being employed, for example for use as a topical agent in an ointment, cream, or similar suspension.

Small molecule (drug): A molecule, typically with a molecular weight less than 1000 Daltons, or in some embodiments, less than about 500 Daltons, which in particular embodiments, is a pharmaceutical compound or drug capable of biological effect, such as analgesia or anti-inflammation.

Subject: Living multi-cellular organisms, including vertebrate organisms, a category that includes both human and non-human mammals.

Under conditions sufficient for [carrying out a desired activity]: A phrase that is used to describe any environment that permits the desired activity.

Wound: An injury to living tissue which can, but does not require breaking skin or bleeding. Particular non-limiting examples of wounds include bruises, burns, and cuts (of varying depths and severity). Wounds can be unintentional, such as resulting from a fall, but can also be intentional, such as a result of surgery or other medical procedure.

Wound dressing: Any covering of any material used to cover a wound. In particular embodiments, wound dressings can be of natural or synthetic fabrics. In other embodiments, wound dressings can be films composed of or including the described compositions. In particular embodiments, a wound dressing does not include any active material. In other embodiments, a wound dressing includes the described compositions, alone, or with other therapeutic agents.

II. Metal Oxide Nanocomposites with Drug-Polymer Conjugate Coatings

Provided herein are metal oxide nanocomposite compositions that include three primary components: (a) a metal oxide nanocomposite; (b) a hemostatic polymer coating the nanocomposite; and (c) a pharmaceutical agent that is conjugated to the polymer coating. The described compositions are ideal for methods of wound care and/or inhibiting microbial infection which benefit from the multivalent therapeutic properties of the described compositions to be antimicrobial, hemostatic, and provide a pharmaceutical agent to a subject.

Metal Oxide Nanocomposites

The metal oxide nanocomposite for use in the described compositions is a semiconductor nanomaterial composition that includes metal oxide A and metal oxide B independently selected from a group comprising an alkaline earth metal, a d-block transition metal, f-block metal or combinations thereof; wherein the nanomaterial comprises clusters of metal oxide quantum dots, and wherein the hemostatic polymer is adhered or coated on the metal oxide semiconductor nanomaterial. These combinations of metal oxides semiconductor nanomaterial and the hemostatic polymer provide many beneficial attributes such as a narrow optical band-gap, inhomogeneous electrical conductivity, a porous structure, relatively large surface area per unit of mass, a large surface area per unit of volume, and coagulation properties. The nanomaterials additionally release reactive oxygen species such that these nanomaterials exhibit antimicrobial properties, antibacterial properties, antifungal properties, or combinations thereof.

The metal oxide semiconductor nanomaterial, described below, comprises at least two metal oxides, metal oxide A and metal oxide B. These nanomaterials comprise clusters of metal oxide quantum dots.

The metal oxide semiconductor nanomaterial comprises a metal oxide A and a metal oxide B wherein the nanomaterial are clusters of metal oxide quantum dots.

A wide variety of metal oxides may be used as metal oxide A and metal oxide B. In various embodiments, metal oxide A and metal oxide B wherein the metal portion of metal oxide A and the metal portion of metal oxide B are independently selected from a group comprising an alkaline earth metal, a d-transition metal, f-transition, or combinations thereof. Non-limiting examples of suitable metal portion of alkaline earth metal oxides may be beryllium, magnesium, calcium, strontium, or barium. Non-limiting examples of the metal portion of suitable transition metal oxides may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide or zinc.

In preferred embodiments, metal oxide A and metal oxide B wherein the metal portion of metal oxide A and the metal portion of metal oxide B are independently selected from a group consisting of titanium, manganese, nickel, silver, calcium, magnesium, zinc, copper, or combinations thereof.

In particularly preferred embodiments, metal oxide A and metal oxide B wherein the metal portion of metal oxide A and the metal portion of metal oxide B are independently selected from a group consisting of zinc (ZnO), copper (CuO), or combinations thereof. The copper-zinc mixed oxide nanomaterial has a chemical formula of $CuO_{(1-x)}ZnO_x$, wherein x is the atomic ratio of the zinc oxide impurities on the nanomaterial. Generally, the value of x may range from about 0.01 to about 0.26. In various, the value of X may range from about 0.01 to about 0.26, or from about 0.03 to about 0.24. In a preferred embodiment, the value of x may be around 0.2. The crystalline structure of the copper oxide and/or the copper-zinc mixed oxide $CuO_{(1-x)}ZnO_x$ is modified tenorite. In the modified tenorite structure, zinc oxide clusters may intercalate some of copper oxide crystal lattice as interstitial impurities. Tenorite is the crystal structure of copper oxide CuO.

The crystal structure of the metal oxide can be determined by method known in the art. Non-limiting methods for determination of the crystal structure may be Raman spectrometry, high resolution transition electron microscopy (HR-TEM/EDS), x-ray crystallography, or combinations thereof.

As appreciated by the skilled artisan, the nanomaterial for use in the described compositions comprises two regions, where one region is the surface region and the second region is the core region of the nanomaterial. Preferably, the surface region of the nanomaterial completely encloses the core region of the nanomaterial. The distribution of these metal oxides can and will vary. In one embodiment, metal oxide A is substantially distributed in the core region of the nanomaterial while metal oxide B is substantially distributed in the surface region. In another embodiment, metal oxide A is substantially distributed in the surface region of the nanomaterial while metal oxide B is substantially distributed in the core region.

In various embodiments, metal oxide A is substantially distributed in the core region of the nanomaterial while metal oxide B is substantially distributed in the surface region. Generally, the surface region comprises more than 10% by weight of metal oxide B and less than 90% by weight of metal oxide A. In various embodiments, the surface region comprises more than 10% by weight, more than 20% by weight, or more than 25 weight % of metal oxide B. The core region comprises less than 90% by weight of metal oxide A. In various embodiments, the core region comprises less than 90% by weight, less than 80% by weight, or less than 75% by weight of metal oxide A. In a preferred embodiment, the surface region comprises about 27%±3% by weight of metal oxide B and the core region comprises 73%±3% by weight of metal oxide A.

In other embodiments, metal oxide A is substantially distributed in the surface region of the nanomaterial while metal oxide B is substantially distributed in the core region. In general, the surface region comprises more than 80% by weight of metal oxide A. In various embodiments, the surface region comprises more than 80% by weight, more than 85% by weight, or more than 90% by weight of metal oxide A. The core region comprises less than 20% by weight of metal oxide B. In various embodiments, the core region comprises less than 20% by weight, less than 15% by weight, or less than 10% by weight. In a preferred embodiment, the surface region comprises about 93%±1% of metal oxide A and the core region comprises about 9%±1% of metal oxide B. In particular embodiments metal oxide A is CuO and metal oxide B is ZnO. In other particular embodiments, metal oxide A is ZnO and metal oxide B is CuO.

The distribution of the metal oxide B and metal oxide A in the metal oxide semiconductor nanomaterial may be determined by characterization methods known in the art. Non-limiting examples of suitable characterization methods may be scanning electron microscopy (SEM), energy-dispersion X-ray spectroscopy (EDS), transmission electron microscopy (TEM), or combination thereof.

As appreciated by the skilled artisan, a mixture of the nanomaterials may be present in the composition. Overall, the mass content of metal oxide B in the nanomaterial may range from about 10% by weight to about 30% by weight. In various embodiments, the mass content of metal oxide B in the nanomaterial may range from about 10% to about 30% by weight or from about 15% by weight to about 25% by weight. In a preferred embodiment, the mass content of metal oxide B in the nanomaterial may be about 18%±4% by weight.

The metal oxide nanomaterial is a semiconductor. The semiconductor comprises at least one n-type metal oxide nanoparticle and at least one p-type nanoparticle. As appreciated by the skilled artisan, an n-type metal oxide is a semiconductor metal oxide in which most charge carriers are electrons, whereas a p-type metal oxide is a semiconductor metal oxide in which most charge carriers are electron holes. Preferably, the metal oxide semiconductor nanomaterial comprises heterojunctions unions between the n-type and the p-type semiconductors. As appreciated by the skilled artisan, heterojunctions are interfaces between two dissimilar crystalline semiconductors which have unequal band gaps.

The metal oxide semiconductor nanomaterial shows an inhomogeneous electrical conductivity. The inhomogeneous electrical conductivity may be the result of an inhomogeneous distribution of the metal oxide B in the surface region of the metal oxide semiconductor nanomaterial or may be result from an inhomogeneous distribution of the metal oxide A in the surface region of the metal oxide semiconductor nanomaterial.

Quantum dots exhibit properties that are an intermediate between those of bulk semiconductors and those of discrete atoms or molecules. Quantum dots are very small semiconductor particles having nanometer size. Quantum dots are also semiconductor nanocrystals. The semiconductor nanomaterials of the present invention comprise semiconductor particles of nanometer size, nanocrystals, or combinations thereof. In other words, any semiconductor metal oxide may be synthesized as quantum dots.

The described metal oxide nanomaterial exhibits many useful and unique properties.

Generally, the optical band gap of the metal oxide semiconductor nanomaterial may range from about 0.5 eV to 6.5 eV. In various embodiments, the optical band gap of the metal oxide semiconductor nanomaterial may range from about 0.5 eV to 6.5 eV, from about 1.0 eV to 4.0 eV, from about 1.2 eV to 2.1 eV, or from about 1.74 eV to 1.85 eV. In a preferred embodiment, the optical band gap of the metal oxide semiconductor nanomaterial may be about 1.8 eV.

The metal oxide semiconductor nanomaterial comprises a mesoporous structure at a nanometer scale, a large surface area per unit of mass (m2/g), a large surface area per unit of volume (m2/mL), or combinations thereof. Generally, the surface area of the metal oxide semiconductor nanomaterial may be larger than 20 m2/g. In various embodiments, the surface area of the metal oxide semiconductor nanomaterial may be larger than about 20 m2/g, or larger than about 40 m2/g. In a preferred embodiment, the surface area of the metal oxide semiconductor nanomaterial may range from about 40 m2/g.

Generally, the size of or at least one dimension of metal oxide semiconductor nanoparticle may range from about 1 nanometer to 1,000 nanometers. In various embodiments, the size of or at least one dimension of metal oxide semiconductor nanoparticle may range from about 1 nanometer to 1,000 nanometers, from about 10 nanometers to about 1,000 nanometers, or from about 100 nanometers to about 1,000 nanometers, or any size in between. In a preferred embodiment, the size of or at least one dimension of metal oxide semiconductor nanoparticle may range from about 10 nanometers to about 150 nanometers.

In general, the thickness of the surface region may range from about 1 nm to about 1000 nm. In various embodiments, the thickness of the surface area may range from about 1 nm to about 1000 nm, from about 10 nm to about 50 nm, or from about 15 nm to about 45 nm. In a preferred embodiment, the thickness of the surface region may be about 30 nm.

The metal oxide semiconductor nanomaterial exhibits antimicrobial properties, antibacterial properties, antifungal properties, or a combination thereof. These metal oxide semiconductor nanomaterials release reactive oxygen species once in contact with a microorganism, a bacterium, or a fungus. Non-limiting examples of reactive oxygen species may be oxygen, a superoxide anion, a peroxide anion, a hydroxyl radical, or combinations thereof. These reactive oxygen species, once in contact with a microorganism, a bacterium, or a fungus can cause damage to cells through oxidative damage. These metal oxide semiconductor nanomaterials present positively charge surface, which might interact with the negatively charged bacterial membrane and cause physical damage and membrane permeability disruption by electrostatic interactions with the microorganism.

The antimicrobial properties, including antibacterial properties, antifungal properties, antiviral properties, or a combination thereof of the metal oxide semiconductor nanomaterials is defined as a bactericidal effect expressed as percentage of mortality against a specific kind of bacteria for a specific duration of time in a specific concentration. Generally, the average of mortality rate of the nanomaterial against *Escherichia coli* over from 1 to 24 hour time period may be larger than about 50%. In various embodiments, the average mortality rate of the nanomaterial against *Escherichia coli* over an hour time period may be larger than about 90%, larger than about 95%, larger than 99%, larger than about 99.9%, or larger than 99.99%. In a preferred embodiment, the average mortality rate of the nanomaterial against *Escherichia coli* over an hour time period may be larger than about 99.99%.

Hemostatic Polymer Coating

The nanocomposite compositions described herein include at least one polymer material, at least one organic molecule, or combinations thereof, which coat the nanocomposite described above. In particular embodiments, the nanomaterial may be dispersed in the at least one polymer, at least one organic molecule, or combinations thereof. In other embodiments, the metal oxide at the surface of the nanomaterial may be functionalized with the at least one polymer, at least one organic molecule, or combinations thereof. In either case, the metal oxide semiconductor nanomaterial may be used in many different applications and environments.

A wide variety of polymer materials and organic molecules may be used with the metal oxide nanomaterial. Non-limiting examples of suitable polymer materials for use in the described compositions include chitosan and derivatives thereof, calcium salt of alginate and divalent cation alginate derivatives thereof, polylysine, or oxidized cellulose. Particular examples of such polymers include chitosan, alginate, gelatin, carboxymethyl cellulose, polyethylene glycol, or combinations thereof. Non-limiting examples of suitable organic molecules may be octadecanethiol, perfluorothiol, cysteine, mercaptoalkanes, citric acid, oleic acid, or combinations thereof.

In one preferred embodiment, the at least one polymer is a hemostatic polymer. Non-limiting examples of hemostatic polymers may be chitosan, alginate, gelatin, carboxymethyl cellulose, polyethylene glycol, collagen, alginic acid, poly(cyanacrylate)s, (polyalkylene oxide)s, or salts thereof.

Generally, the weight % (wt %) of the at least one polymer material, at least one organic molecule, or combinations thereof dispersed or functionalized on the metal oxide semiconductor nanomaterial may range from about 1 wt % to about 10 wt % of the metal oxide nanocomposite. In various embodiments, the weight % (wt %) of the at least one polymer material, at least one organic molecule, or combinations thereof dispersed or functionalized on the metal oxide semiconductor nanomaterial may range from about 1 wt % to about 10 wt %, from about 2 wt % to about 8 wt %, or from about 2.5 wt % to about 3.5 wt %. In one preferred embodiment, the weight (wt %) of the at least one polymer material, at least one organic molecule, or combinations thereof dispersed or functionalized on the metal oxide semiconductor nanomaterial may be about 3 wt %.

In general, the thickness of the at least one polymer, at least one organic molecule, or combinations thereof may range from about 1.0 nm to about 10.0 nm. In various embodiments, the thickness of the at least one polymer, at least one organic molecule, or combinations thereof may range from about 1.0 nm to about 10.0 nm, from about 2.0 nm to about 8.0 nm, or from about 3.0 to about 6.0 nm.

The coated or adhered metal oxide semiconductor nanomaterial with at least one polymer, at least one organic molecule, or combinations thereof exhibit unique properties. In one preferred embodiment, the at least one polymer, at least one organic molecule, or combinations thereof may be a hemostatic polymer. Specific hemostatic polymers are described above. The hemostatic polymer provides additional attributes such as blood coagulation. The surface ζ-potential for 100 ppm water suspension of chitosan functionalized or coated on the metal oxide semiconductor nanomaterial may range from +10 mV to about +30 mV. In various embodiments, the surface ζ-potential for 100 ppm water suspension of chitosan functionalized or coated on the metal oxide semiconductor nanomaterial may range from +10 mV to about +30 mV, from about +15 mV to about +25 mV, or about +20 mV.

The surface ζ-potential for 100 ppm water suspension of calcium alginate functionalized or coated on the metal oxide semiconductor nanomaterial may range from −40 mV to about 0 mV. In various embodiments, the surface ζ-potential for 100 ppm water suspension of calcium alginate functionalized or coated on the metal oxide semiconductor nanomaterial may range from −40 mV to about 0 mV, from about −30 mV to about −10 mV, or about −20 mV.

The antimicrobial activity for the hemostatic polymer coated or adhered on the metal oxide semiconductor nanomaterial in a 40 ppm suspension of *Escherichia coli* may be at least 95%. In various embodiments, the antimicrobial activity for the hemostatic polymer dispersed or functionalized on the metal oxide semiconductor nanomaterial in a 40 ppm suspension of *Escherichia coli* may be at least 95%, at least 97.5%, at least 99%, or at least 99.999%. In one preferred embodiment, the antimicrobial activity for the hemostatic polymer coated or adhered on the metal oxide semiconductor nanomaterial in a 40 ppm suspension of *Escherichia coli* is at least 99.999% or not less than a 5 log reduction.

Pharmaceutical Drugs Conjugated to the Hemostatic Polymer

As noted, the described nanocomposite compositions include a hemostatic polymer layer to which is conjugated a pharmaceutical agent. In particular embodiments, the pharmaceutical agent can be conjugated to the polymer before the polymer is combined with the metal oxide nanocomposite to produce a polymer-coated nanomaterial. In other embodiments, the pharmaceutical agent can be conjugated to the polymer after it has coated the metal oxide nanomaterial. Conjugation of the pharmaceutical agent to the hemostatic polymer is carried out by standard methods, which can, in particular embodiments, be adjusted by increasing or decreasing the pH of the reaction above 7, such as 8 or 9. In particular embodiments, the pharmaceutical agent is conjugated to the polymer through a covalent interaction. In other embodiments, the pharmaceutical agent is conjugated to the polymer through a non-covalent interaction such as an electrostatic interaction.

The pharmaceutical agents from used in the described compositions can include any biologically active molecule, such as a pharmaceutical compound (e.g., a small molecule drug) or a biomolecule such as a polynucleotide, polypeptide, or antibody.

Particular non-limiting examples of pharmaceutical compounds that can be conjugated to the polymer in the described nanocomposite composition include an analgesic compound, local anesthetic, anti-inflammatory agent, non-steroidal anti-inflammatory drug (NSAID) (which can combine analgesia and anti-inflammatory functionalities), opioid, and/or a topical antibiotic. Non-limiting examples of analgesic compounds include aspirin, acetaminophen, and derivatives thereof. Non-limiting examples of anesthetics include tetracaine, procaine, lidocaine, and borneol. Non-limiting examples of NSAIDs include Ibuprofen, diclofenac, ketorolac, and meloxicam. Non-limiting examples of antibiotics include β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim.

In further particular embodiments, the pharmaceutically-active drug is an analgesic and/or anti-inflammatory drug selected from tetracaine, tetracaine hydrochloride, procaine, procaine hydrochloride, ibuprofen, lidocaine, diclofenac, acetaminophen, and aspirin.

Processes for Preparing the Metal Oxide Semiconductor Nanomaterial

In another aspect, disclosed herein, are processes to prepare the metal oxide semiconductor nanomaterial. The process comprises: (a) providing a first aqueous solution comprising a soluble metal salt A and a soluble metal salt B; (b) providing a second aqueous solution comprising at least one soluble anion; (c) admixing the second aqueous solution with the first aqueous solution to form an insoluble precursor metal oxide semiconductor nanomaterial; (d) isolating the metal oxide semiconductor nanomaterial precursor; (e) drying the metal oxide semiconductor precursor; (f) thermal decomposition of the metal oxide semiconductor precursor to form the metal oxide semiconductor nanomaterial; (g) coating or adhering the conjugate of hemostatic polymer and drug on the surface of the metal oxide semiconductor nanomaterial; and (h) drying the hemostatic polymer and drug conjugate coated or adhered on the metal oxide semiconductor nanomaterial. The process may be conducted in batch, semi-continuous, or continuous mode.

(a) First Aqueous Solution

The process commences by preparing the first aqueous solution comprising a soluble metal salt A and a soluble metal salt B.

As appreciated by the skilled artisan, the soluble metal salts A and B are transformed into metal oxide A and metal oxide B after completion of the process.

A wide variety of soluble metal salts may be used in the process to prepare metal oxide A and metal oxide B. In various embodiments, soluble metal salt A and soluble metal salt B wherein the metal portion of these salts are independently selected from a group comprising an alkaline earth metal, a transition metal, or combinations thereof. Non-limiting examples of suitable metal portion of alkaline earth metal salts may be beryllium, magnesium, calcium, strontium, or barium. Non-limiting examples of the metal portion of suitable transition metal salts may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide, or zinc.

In preferred embodiments, soluble metal salt A and soluble metal salt B wherein the metal portion of these salts are independently selected from a group consisting of titanium, manganese, nickel, silver, calcium, magnesium, zinc, copper, or combinations thereof.

In particularly preferred embodiments, soluble metal salt A and soluble metal salt B wherein the metal portion of these salts are independently selected from a group consisting of zinc, copper, or combinations thereof.

A wide variety of anions may be used for soluble metal salt A and soluble metal salt B. An important aspect of these anions is that the anion is readily exchangeable, soluble in aqueous solution, non-toxic, pH neutral, and thermally decomposable. Non-limiting examples of suitable anions may be acetate, propionate, any soluble organic salt or combinations thereof. In a preferred embodiment, the anions used for soluble metal salt A and soluble metal salt B is acetate.

In other embodiments, the first aqueous solution may further comprise one or more different soluble salts than the soluble salts A and soluble salts B as described above. The molar ratio of the soluble metal salt A to the soluble metal salt B may range from about 12:1 to about 1:12. In various embodiments, the molar ratio of the soluble metal salt A to the soluble metal salt B may range from about 12:1 to about 1:12, from about 11:1 to about 1:11, from about 10:1 to about 1:10, from about 9:1 to about 1:9, from about 8:1 to about 1:8, from about 7:1 to about 1:7, from about 7:1 to about 1:7, from about 6:1 to about 1:6, from about 5:1 to about 1:5, from about 4:1 to about 1:4, from about 3:1 to about 1:3, or from about 2:1 to about 1:2. In a preferred embodiment wherein soluble metal salt A is copper and the soluble metal salt B is zinc, the molar ratio may be about 2.3:1.

In general, the concentration of soluble metal salt A, soluble metal salt B, or combinations thereof in water may range from about 0.01M (moles/liter) to about 1.0M. In various embodiments, the concentration of the soluble metal salt A and soluble metal salt B may range from about 0.01M to about 1.0M, 0.03M to about 0.3M, or from 0.05M to 0.15M. In a preferred embodiment, the concentration of soluble metal salt A, soluble metal salt B, or combinations thereof in water may be about 0.15M.

The first aqueous solution may further comprise a stabilizer. Non-limiting examples of stabilizers may be a polyethylene glycol (PEG), polypropylene glycol (PPG), polyvinylpyrrolidone (PVP), polyvinylalcohol (PVA), Polyoxyethylene or combinations thereof. In a preferred embodiment, the stabilizer used in the first aqueous solution further comprises PEG, specifically PEG4000.

The concentration of the stabilizer in the first aqueous solution may range from about 0.0001M to about 0.001M. In various embodiments, the concentration of the stabilizer in the first aqueous solution may range from about 0.0001M to about 0.001M. In a preferred embodiment, the concentration of the stabilizer in the first aqueous solution may be preferably about 0.0007M.

The preparation of the first solution may be achieved by blending the soluble metal salt A, soluble metal salt B, water, an optional stabilizer, and an optional solvent in any known mixing equipment or reaction vessel until the mixture achieves homogeneity. These components may be added all at the same time, sequentially, or in any order.

In general, the preparation of the first aqueous solution may be conducted at a temperature that ranges from about 10° C. to about 40° C. In various embodiments, the temperature of the reaction may range from about 10° C. to about 40° C., from about 15° C. to about 35° C., or from about 20° C. to about 30° C. In one embodiment, the temperature of the reaction may be about room temperature (~23° C.). The reaction typically is performed under ambient pressure. The reaction may also be conducted under an inert atmosphere or air, for example under nitrogen, argon or helium.

The duration for preparing the first aqueous solution and will vary depending on many factors, such as the temperature, the method of mixing, and amount of materials being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours. In various embodiments, the preparation may be allowed to continue until the first aqueous solution obtains homogeneity.

(b) Second Aqueous Solution

The second aqueous solution comprises at least one soluble anion source. An important aspect of these soluble anions is that anion is readily exchangeable, soluble in aqueous solution, is non-toxic, pH neutral, and thermally decomposable. Non-limiting examples of suitable anion sources may be lithium bicarbonate, sodium bicarbonate, potassium bicarbonate, and ammonium bicarbonate, or any alkaline oxalate, alkaline malate. In a preferred embodiment, the second aqueous solution comprises ammonium bicarbonate.

The second aqueous solution may be prepared by forming a reaction mixture comprising at least one soluble anion source, water, and optionally ethanol. These components may be added all at the same time, sequentially, or in any order. The second aqueous solution may be achieved by blending the above components in any known mixing equipment or reaction vessel until the mixture achieves a clear solution.

In general, the preparation of the second aqueous solution may be conducted at a temperature that ranges from about 10° C. to about 40° C. In various embodiments, the temperature of the preparation may range from about 10° C. to about 40° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The duration for preparing the second aqueous solution and will vary depending on many factors, such as the temperature, the method of mixing, and amount of the at least one anion source being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours.

Generally, the concentration of the at least one soluble anion source in the second aqueous solution may range from a concentration of about 0.10M to about 1.5M. In various embodiments, the concentration of the at least one soluble anion source in the second aqueous solution may range in a concentration from about 0.10M to about 1.5M, from about 0.2M to about 1.4M, or from about 0.3M to about 1.2M. In a preferred embodiment, the concentration of the at least one soluble anion source in the second aqueous solution may be about 0.3M.

(c) Preparation of the Insoluble Metal Oxide Semiconductor Nanomaterial Precursor.

The next step in the process is to prepare the insoluble metal oxide semiconductor nanomaterial precursor. Preparing the insoluble metal oxide semiconductor nanomaterial precursor occurs when the second aqueous solution comprising the at least one anion source is admixed with the first aqueous solution. As appreciated by the skilled artisan, once the second aqueous solution is admixed with the first aqueous solution, a chemical reaction occurs. In a preferred embodiment, the metal oxide semiconductor nanomaterial precursor comprising a copper zinc mixed carbonates are formed and can be depicted according to the following scheme.

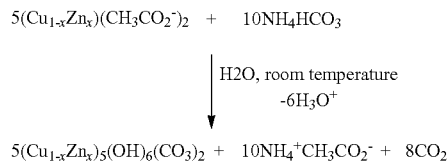

As appreciated by the skilled artisan, an advantage of using ammonium salt in the second aqueous solution is that by product, ammonium acetate, is water soluble, easily removed from the metal oxide semiconductor nanomaterial precursor, neutral pH at room temperature, and trace amount of ammonium acetate are readily thermally decomposed in the process.

The process may further comprise an organic solvent. The purpose of the solvent in the process is to reduce the foaming as the two aqueous solutions are combined, namely carbon dioxide. The addition of solvent may also cause a sudden change of the dielectric constant and change the dynamic of precipitation of the insoluble metal oxide semiconductor nanomaterial precursor. These changes may further lead to a hierarchic structure, a core-shell configuration of the metal oxide semiconductor nanomaterial, or combinations of both of properties. An additional property of the solvent is that solvent is volatile so excess amounts of solvent may be readily removed. Non-limiting examples of suitable solvents may be methanol, ethanol, propanol, iso-propanol, acetone or combinations thereof. In a preferred embodiment, the solvent in the process is ethanol.

Generally, the volume percent of the solvent in the mixture of the first aqueous solution, the second aqueous solution or combinations thereof may range from about 0.01 volume % to about 0.1 volume % In various embodiments, the volume percent of the solvent in the mixture of the first aqueous solution, the second aqueous solution or combinations thereof may range from about 0.01 volume % to about 0.1 volume %, from about 0.02 volume % to about 0.08 volume %, or from about 0.03 volume % to about 0.07 volume %. In a preferred embodiment, the volume percent of the solvent in the mixture of the first aqueous solution, the second aqueous solution or combinations thereof may be about 0.02 volume %.

The solvent may be added to the first aqueous solution, the second aqueous solution, or the combination of the first aqueous solvent and the second aqueous solvent, or combinations thereof.

The metal oxide semiconductor nanomaterial precursor may be prepared by forming a reaction mixture comprising the first aqueous solution, the second aqueous solution, and the optional solvent. The metal oxide semiconductor nanomaterial precursor may be achieved by blending the above components in any known mixing equipment or reaction vessel or static mixer until the mixture achieves completeness of reaction.

In an embodiment, the second aqueous solution may be added to the first solution. Generally, the second aqueous solution is added immediately in a batch o by a static mixer continuously in a range from about 20 volume % to about 45 volume % to the first aqueous solution. In a speed from 1 to 10 l/min, in various embodiments from 1.25 to 8l/min. In a preferred embodiment 5 to 6 l/min. This quick addition ensures the chemical reaction depicted above goes to completion.

Since the insoluble metal oxide semiconductor nanomaterial precursor precipitates from an aqueous solution, the method of stirring to prepare the precursor is important so amounts of the soluble metal salt A, metal salt B, or the at least one soluble anion source does not become entrained in the insoluble metal oxide semiconductor nanomaterial precursor. Generally, the process may be stirred mechanically at a speed from about 250 rpm (revolution per minute) to about 1000 rpm. In various embodiments, the stiffing speed may range from 250 rpm to about 1200 rpm, from about 300 rpm to about 1000 rpm, or from about 500 rpm to about 900 rpm. In a preferred embodiment, the stirring speed of the process may be about 700 rpm.

In general, the preparation of the insoluble metal oxide semiconductor nanomaterial precursor may be conducted at a temperature that ranges from about 10° C. to about 65° C. In various embodiments, the temperature of the preparation may range from about 10° C. to about 65° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The pH during the addition of the reaction between the second aqueous solution and the first aqueous solution may range from about 6.0 to about 8.0. In various embodiments, the pH of the process may range from about 6.0 to about 8.0, from about 6.5 to about 7.5, or from about 6.7 to about 7.3. In a preferred embodiment, the pH of the process is about 6.8 to 7.0. The duration for preparing the insoluble metal oxide semiconductor nanomaterial precursor and will vary depending on many factors, such as the temperature, the method of mixing, and scale of the process. The duration of the reaction may range from about 5 minutes to about 6 hours. In some embodiments, the duration of the reaction may range from about 5 minutes to about 6 hours, from about 15 minutes to about 4 hours, or from about 20 minutes to about 1 hour. In a preferred embodiment, the duration for preparing the insoluble metal oxide semiconductor precursor may be about 30 minutes.

(d) Isolating the Insoluble Metal Oxide Semiconductor Nanomaterial Precursor

The next step in the process is isolating the insoluble metal oxide semiconductor nanomaterial precursor from the reaction mixture in step (c) comprising water, the stabilizer, and the optional solvent. As appreciated by the skilled artisan, there are many methods of isolating the insoluble metal oxide semiconductor nanomaterial precursor from the reaction mixture in step (c). Non-limiting methods may be filtration, centrifugal separation, decantation, or combinations thereof. The insoluble metal oxide semiconductor nanomaterial precursor, after isolation, may be rinsed with water, ethanol, or combinations thereof. The precursor is washed with water, ethanol, or combinations thereof solvent until the supernatant is colorless or the precursor color remains constant.

(e) Drying the Insoluble Metal Oxide Semiconductor Precursor.

The next step in the process is drying the insoluble metal oxide semiconductor nanomaterial precursor from the reaction mixture in step (d). This step would remove excess amounts of solvent from the insoluble metal oxide semiconductor nanomaterial precursor. As appreciated by the skilled artisan, many devices are available to dry the precursor. Non-limiting examples for drying the solid may be batch driers, convection ovens, rotary dryers, drum dryers, kiln dryers, flash dryers, or tunnel dryers.

In general, the drying of the insoluble metal oxide semiconductor nanomaterial precursor may be conducted at a temperature that ranges from about 30° C. to about 120° C. In various embodiments, the temperature of the preparation may range from about 30° C. to about 120° C., from about 40° C. to about 100° C., or from about 50° C. to about 80° C. In one embodiment, the temperature of drying may be about 60° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 30 minutes to about 48 hours. In some embodiments, the duration of the reaction may range from about 30 minutes to about 48 hours, from about 1 hour to about 24 hours, or from about 2 hours to about 4 hours. In a preferred embodiment, the duration for drying the insoluble metal oxide semiconductor precursor may be about 3 hours, or until the drying the insoluble metal oxide semiconductor precursor reaches less than 12% moisture.

(f) Thermal Decomposition of the Insoluble Metal Oxide Semiconductor Nanomaterial Precursor Forming the Metal Oxide Semiconductor Nanomaterial The next step in the process is thermal decomposition of the insoluble metal oxide semiconductor nanomaterial precursor forming the metal oxide semiconductor nanomaterial. This step removes transforms the thermally labile ligand forming the oxides and removes by-products and impurities that were not removed in step (d). As appreciated by the skilled artisan, carbon, hydrogen and excessive oxygen may be released in forms of carbon dioxide and water steam from the thermally labile ligands, by-products, and impurities. In a preferred embodiment, the metal oxide semiconductor nanomaterial precursor comprising a copper zinc mixed oxide is thermally decomposed to form the metal oxide semiconductor nanomaterial. This reaction can be depicted according to the following scheme.

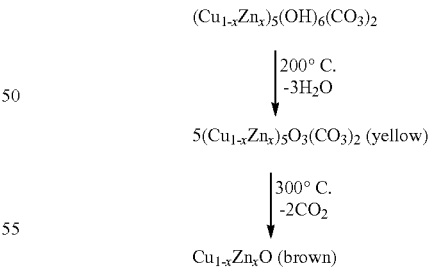

In general, thermal decomposition of the insoluble metal oxide semiconductor nanomaterial precursor may be conducted at a temperature that ranges from about 200° C. to about 1000° C. In various embodiments, the temperature of the preparation may range from about 200° C. to about 1000° C., from about 225° C. to about 800° C., or from about 250° C. to about 350° C. In one embodiment, the temperature of drying may be about 300° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 5 minutes to about 48 hours. In some embodiments, the duration of the reaction may range from about 10 minutes to about 48 hours, from about 15 hours to about 24 hours, or from about 2 hours to about 4 hours. In a preferred embodiment, the duration for drying the insoluble metal oxide semiconductor precursor may be about 0.3 hour.

The yield of the metal oxide semiconductor material from the process described above may range from 5 to 12 g/L. with high purity.

(g) Coating or Functionalizing the Hemostatic Polymer on the Surface of the Metal Oxide Semiconductor Nanomaterial The process further comprises coating or adhering a hemostatic polymer on the metal oxide semiconductor surface. Various hemostatic polymers are described above. Method for coating or adhering the hemostatic polymer on the metal oxide semiconductor nanomaterial are known in the arts. In one embodiment, the hemostatic polymer may be dispersed with the metal oxide semiconductor nanomaterial, thereby coating or adhering the hemostatic polymer to the surface of the metal oxide semiconductor nanomaterial.

As described herein, the hemostatic polymer is loaded with a pharmaceutical agent, either prior to coating on the nanomaterial or after coating. Loading of the pharmaceutical agent is done following solubilizing of the hemostatic polymer and carried out at neutral pH or an adjusted pH, according to the polymer and drug to be loaded. In particular embodiments, the pharmaceutical agent is loaded onto the polymer at pH 7. In other embodiments, the pharmaceutical agent is loaded onto the polymer at pH 8 or 9.

The efficiency of loading the drug onto the polymer can be from 10% to 90%, such as at least 10%, 20%, 30%, 40%, 50%, 60%, 70%, 80%, 90% or even greater.

Generally, the weight % (wt %) of the hemostatic polymer on the metal oxide semiconductor nanomaterial surface may range from about 1 wt % to about 5 wt %. In various embodiments, the weight % (wt %) of the hemostatic polymer dispersed on the metal oxide semiconductor nanomaterial surface may range from about 1 wt % to about 5 wt %, from about 2 wt % to about 4 wt %, or from about 2.5 wt % to about 3.5 wt %. In one preferred embodiment, the weight % (wt %) of the hemostatic polymer on the metal oxide semiconductor nanomaterial surface may be about 3 wt %.

(h) Drying the Hemostatic Polymer Coated on the Metal Oxide Semiconductor Nanomaterial The process optionally further comprises drying the hemostatic polymer coated or adhered on the surface of the metal oxide semiconductor nanomaterial. This step would remove excess amounts of solvent/water from the hemostatic polymer coated metal oxide semiconductor nanomaterial. As appreciated by the skilled artisan, many devices are available to dry the precursor. Non-limiting examples for drying the solid may be batch driers, convection ovens, rotary dryers, drum dryers, kiln dryers, flash dryers, or tunnel dryers.

In general, the drying of the hemostatic polymer coated or adhered on the metal oxide semiconductor nanomaterial may be conducted at a temperature that ranges from about 30° C. to about 120° C. In various embodiments, the temperature of the preparation may range from about 30° C. to about 120° C., from about 40° C. to about 100° C., or from about 50° C. to about 80° C. In one embodiment, the temperature of drying may be about 60° C. The preparation typically is performed under ambient pressure. The preparation may also be conducted under air or an inert atmosphere, for example under nitrogen, argon or helium.

The duration for drying the hemostatic polymer coated or adhered to the metal oxide semiconductor nanomaterial surface can and will vary depending on many factors, such as the temperature, the amount of the hemostatic polymer, and the type of the dryer. The duration of the reaction may range from about 30 minutes to about 48 hours. In some embodiments, the duration of the drying may range from about 30 minutes to about 48 hours, from about 1 hour to about 24 hours, or from about 2 hours to about 4 hours. In a preferred embodiment, the duration for drying of the hemostatic polymer coated metal oxide semiconductor nanomaterial may be about 3 hours to 6 hours.

Methods for Using the Metal Oxide Semiconductor Nanomaterial

In still another aspect, disclosed herein are methods of using the metal oxide semiconductor nanomaterial or the metal oxide semiconductor nanomaterial surface coated or adhered with the drug-conjugated hemostatic polymer. The methods comprise coating an article such as fabrics bandages, coating textiles, catheters, and syringe needles with the metal oxide semiconductor nanomaterial or the metal oxide semiconductor nanomaterial surface coated or adhered to with the drug-conjugated hemostatic polymer, hydrophobic coatings comprising the metal oxide semiconductor nanomaterial, creams for human and animal use, and photovoltaic cells comprising the metal oxide semiconductor nanomaterial. The metal oxide semiconductor nanomaterials described herein may be further incorporated into paints or coatings.

In one embodiment, the method comprises coating an article such as fabric bandages, textiles, catheters, and needles with an effective amount of the metal oxide semiconductor nanomaterial or the metal oxide semiconductor nanomaterial surface coated or adhered with the hemostatic polymer to which is conjugated a pharmaceutical drug. The method comprises dispersing the metal oxide semiconductor nanomaterial or the metal oxide semiconductor nanomaterial surface coated or adhered with the drug-conjugated hemostatic polymer in the appropriate solvent (such as ethanol, water, or combinations thereof), spraying the dispersed metal oxide nanomaterial or the metal oxide semiconductor nanomaterial surface coated or adhered with the drug-conjugated hemostatic polymer onto the article thereby forming a coating of the metal oxide semiconductor nanomaterial or the metal oxide semiconductor nanomaterial surface coated or adhered with the drug-conjugated hemostatic polymer on the coating, and drying the coating to remove the solvent using heat, vacuum, an inert gas. Once the coating is applied to the article, the article provides antimicrobial properties, antibacterial properties, antifungal properties, or combinations thereof to the article, and in certain embodiments, additional pharmaceutical benefits such as but not limited to analgesia and/or anti-inflammation.

In another embodiment, the metal oxide nanomaterial compositions described herein are formulated into a topical cream and then applying the topical cream to a subject to an infected area on the subject. With such low toxicity, the topical cream would provide antimicrobial and additional pharmaceutical properties, including but not limited to antibacterial properties, antifungal properties, antiviral properties, analgesia, or combinations to the subject and eliminating the virus, bacterium, or the fungus.

In still another aspect, the method comprises adding the metal oxide semiconductor nanomaterial or the metal oxide semiconductor nanomaterial surface coated or adhered with the hemostatic polymer to a hydrophobic coating. The method comprises mixing the metal oxide semiconductor nanomaterial or the metal oxide semiconductor nanomaterial surface coated or adhered with the drug-conjugated hemostatic polymer with a hydrophobic coating. After applying this coating to an article, the coating would provide water repellency and antimicrobial properties, antibacterial properties, antifungal properties, or combinations to the article. Non-limiting examples of these articles may be metals, glass, and ceramics used in many applications.

In yet another embodiment, the metal oxide semiconductor nanomaterial may be used in photovoltaic cells. The method comprises adding the metal oxide semiconductor nanomaterial into the photovoltaic cell. With such a narrow bandgap, previously described above, photons from light would be absorbed by the metal oxide semiconductor nanomaterial thereby generating free electrons and electricity.

In still another embodiment, the metal oxide semiconductor nanomaterial or the metal oxide semiconductor nanomaterial surface coated or adhered with the hemostatic polymer may be incorporated into various coatings such as paints and epoxy resins. After application and drying of the paints or epoxy resins, the coating would provide antimicrobial properties, antibacterial properties, antifungal properties, or a combination thereof. These coatings would be useful in a number of areas such as a hospital, a clinic, food industry, plastic, paints, pharmaceutical industry, or cosmetics industry.

The metal oxide semiconductor nanomaterial may be used for chemical catalysis in electrochemical or organic reactions due to its huge surface area and non-homogenous electrical conduction.

In particular embodiments, the metal oxide nanocomposite compositions are formulated as a pharmaceutical composition that includes the described nanocomposite composition and a pharmaceutically-acceptable salt, carrier, or excipient known to the art. The metal oxide nanocomposite compositions, or pharmaceutical compositions thereof, can in certain embodiments, be formulated for administration by first-aid gauze, wound dressing foams and films, topical ointment, or topical spray according to standard methods. The described formulations include therapeutically effective amounts of the described composite composition in lotions, foams, patches, gels, suspensions, and solutions, all of which can be prepared by standard methods of the art and applied to materials for treatment as needed, such as bandages, wound dressings, gauze, and the like.

In other particular embodiments, the metal oxide nanocomposite compositions, or pharmaceutical compositions thereof can be added to a dressing for treatment of a wound. In such methods, the metal oxide nanocomposite compositions, or pharmaceutical compositions thereof contacts the wound site and releases the conjugated drug upon contact with the wound surface.

As noted, the metal oxide nanocomposite compositions, or pharmaceutical compositions thereof are used in methods of treatment of a wound and also methods for inhibiting microbial growth on a subject in need of such treatment. The described methods include administering to or contacting a subject with a therapeutically effective amount of the metal oxide nanocomposite compiolooooooooositions, or pharmaceutical compositions thereof, thereby treating the wound and/or inhibiting microbial growth with the antimicrobial, hemostatic, and/or additional active properties of the compositions. In particular embodiments, the hemostatic polymer is loaded with an analgesic drug. Accordingly, the methods will include pain relief to the subject. In other embodiments, the hemostatic polymer is loaded with an anti-inflammatory drug, which provides such treatment to the subject. In still other embodiments, the conjugated drug is one or more compounds or agents that provide multiple properties such as reduction in pain, inflammation, and/or additional antimicrobial benefits.

The following examples are provided to illustrate certain particular features and/or embodiments. These examples should not be construed to limit the disclosure to the particular features or embodiments described.

EXAMPLES

Example 1: Preparation of the $CuO_{(1-x)}ZnO_x$ Nanomaterial

Into a 20 L reactor equipped with mechanical stiffing was added 200 g Cu(OAc)2 and 12 L deionized water (DI). To this solution was added 110 g Zn(OAc)2 and 5 g PEG 4000. This mixture was stirred until add the solids dissolved. Into a 5 L reactor was added 240 g $NH_4HCO_3$ in 3 L DI water. This mixture was stirred until the solids dissolved. Once the $NH_4HCO_3$ solution becomes homogeneous, the $NH_4HCO_3$ solution is slowly added into the 20 L reactor maintaining the mechanical stiffing at 200 rpm, until foam begins to form. At this time, 30 mL EtOH is added while the addition of the $NH_4HCO_3$ solution continues. After the addition of the $NH_4HCO_3$ solution is complete, the reaction is stirred for an additional 30 minutes where a solid is formed. The solid is filtered using vacuum filtration. The solid was removed, resuspended in 800 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid is annealed for 20 minutes under a flow of nitrogen yielding 120 g of the nanomaterial.

Example 2: Preparation of the $CuO_{(1-x)}ZnO_x$ Nanomaterial at 0.15M (CuO) when x=0

Into a 2 L reactor equipped with mechanical stiffing was added 45 g Cu(OAc)2 and 1.2 L deionized water (DI). To this solution was added 0.5 PEG 4000. This mixture was stirred until add the solids dissolved. Into a 500 mL reactor was added 24 g $NH_4HCO_3$ in 0.3 L DI water. This mixture was stirred until the solids dissolved. Once the $NH_4HCO_3$ solution becomes homogeneous, the $NH_4HCO_3$ solution is slowly added into the 2 L reactor maintaining the mechanical stiffing at 200 rpm until foam begins to form. At this time, 3 mL EtOH is added while the addition of the $NH_4HCO_3$ solution continues. After the addition of the $NH_4HCO_3$ solution is complete, the reaction is stirred for an additional 30 minutes where a solid if formed. The solid is filtered using vacuum filtration. The solid was removed, resuspended in 80 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid was annealed for 20 minutes under a flow of nitrogen yielding 12.0 g of the nanomaterial.

Example 3: Preparation of the $CuO_{(1-x)}ZnO_x$ Nanomaterial at 0.15M (ZnO) when X=1

Into a 2 L reactor equipped with mechanical stiffing was added 49.4 g Zn(OAc)2 and 1.2 L deionized water (DI). To this solution was added 0.5 g PEG 4000. This mixture was stirred until add the solids dissolved. Into a 500 mL reactor was added 24 g $NH_4HCO_3$ in 0.3 L DI water. This mixture was stirred until the solids dissolved. Once the $NH_4HCO_3$ solution becomes homogeneous, the $NH_4HCO_3$ solution is slowly added into the 2 L reactor maintaining the mechanical stiffing at 200 rpm until foam begins to form. At this time, 3 mL EtOH is added while the addition of the $NH_4HCO_3$ solution continues. After the addition of the $NH_4HCO_3$ solution is complete, the reaction is stirred for an additional 30 minutes where a solid if formed. The solid is filtered using vacuum filtration. The solid was removed, resuspended in 80 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid was annealed for 20 minutes under a flow of nitrogen yielding 12.0 g of the nanomaterial.

Example 4: Antibacterial Properties of the $CuO_{(1-x)}ZnO_x$ Nanomaterial

A 200 ppm stock suspension of each nanomaterial tested ($CuO_{(1-x)}ZnO_x$, CuO, ZnO, mix CuO and ZnO, and Zn doped CuO) were prepared by adding 20 mg of particles to 100 mL saline (0.86% NaCl) in a 100 mL volumetric flask. The flask was placed in a sonic bath (Bandelin RK 1028 CH, ultrasonic power 1200 W) and sonicated for 10 minutes.

A bacterial suspension was prepared from cells harvested from a 24 h TSA plate (Tryptic Soya Agar, HiMedia) at 36° C. and suspended in saline. Bacterial concentration in the suspension was measured using a nephelometer (PhoenixSpec, BD) and diluted to 106 cfu/mL.

Suspensions in saline of 20 ml nanoparticles and 10 ml of 106 cfu/mL bacteria were mixed to a final volume of 10 mL, in a 50 mL sterile polypropylene test-tube. The tube was incubated and shaken at a known temperature (24° C./36° C.) for 1 hour. At the end of incubation, a volume of 1 mL was taken from the tube and used for preparation of serial dilutions. 1 mL samples from each dilution were plated with molten TSA using the pour plate method. Plates were incubated at 36° C. for 1 and 24 hours and counted. Giving a killing about 99.99% for NED after 1 h.

Example 5: Preparation of Chitosan Coated $CuO_{(1-x)}ZnO_x$ Nanocomposite

This process was conducted in two steps. In the first step, a water-soluble modified chitosan was prepared. The simplest modification was through synthesis of chitosan mesylate salt or chitosan chloride. Chitosan (1 g) was suspended in water (80 ml) at ~10° C. To this, methane sulfonic acid or HCl (~1 mL) was added dropwise until the solution became clear and was then stirred for an additional hour. Resulting modified chitosan was purified by 48 h dialysis against deionized water.

In the second step, modified chitosan was coated over the nanocomposite. To a suspension of $CuO_{(1-x)}ZnO_x$ nanocomposite in deionized water (7.5 g/L), an aqueous solution of the modified chitosan (2.25 g/L) was added under stiffing. The solution was stirred for 8 h at room temperature. Excess/unbound polymer was removed by centrifugation and the slurry was dried under vacuum to obtain chitosan coated $CuO_{(1-x)}ZnO_x$ Nanocomposite.

Example 6: Preparation of Calcium Alginate Coated on $CuO_{(1-x)}ZnO_x$ Nanocomposite To a suspension of $CuO_{(1-x)}ZnO_x$ nanocomposite in deionized water (7.5 g/L) prepared as described above was added an aqueous solution of Na-Alginate (2.25 g/L) dropwise while stiffing. The solution was stirred for 8 h at room temperature. Excess/unbound polymer was removed by centrifugation to obtain Na-Alginate coated nanoparticle slurry. To prepare Ca-Alginate coated nanoparticles, an ion exchange reaction was performed. To the suspension of Na-alginate coated nanoparticles, aq. $CaCl_2$ (10 g/L) was added dropwise and stirred for 3 h. Excess $CaCl_2$ was removed by centrifugation to get Ca-Alginate coated nanoparticles slurry.

Example 7: Preparation of $CuO_{(1-x)}ZnO_x$ Nanocomposite Coated with Chitosan-Fluorescein Conjugate Fluorescein is a model drug; its loading onto a polymer for coating a $CuO_{(1-x)}ZnO_x$ nanocomposite, and its release from the coated nanocomposite is described in the following steps:

Step 1. In the first step, a water-soluble modified chitosan was prepared. The simplest modification is through synthesis of chitosan mesylate salt or chitosan chloride. Chitosan (1 g) was suspended in water (80 ml) at ~10° C. To this, methane sulfonic acid or HCl (~1 mL) was added dropwise until the solution became clear. The solution was stirred for an additional hour. Resulting modified chitosan was purified by 48 h dialysis against deionized water.

Step 2. In the second step, fluorescein-chitosan conjugate was prepared. Fluorescein (20 mg) was dissolved under basic condition (30 drops of 0.1M NaOH in 20 mL of DIW) and stirred for 3 h. Water soluble chitosan, Chi-HCl (200 mg) was diluted in water (80 mL). The fluorescein solution was added dropwise to Chi-HCl and stirred for 30 min.

Step 3. In the third step, fluorescein-chitosan conjugate was coated over the nanocomposite. $CuO_{(1-x)}ZnO_x$ nanocomposite (2 g) was suspended in DIW (300 mL) under ultrasonication (90%-amplitude, 5 min). To the nanocomposite suspension, fluorescein-chitosan conjugate solution was added dropwise and stirred overnight. The suspension was centrifuged twice at 10,000 rpm for 5 min.

Figure 8:
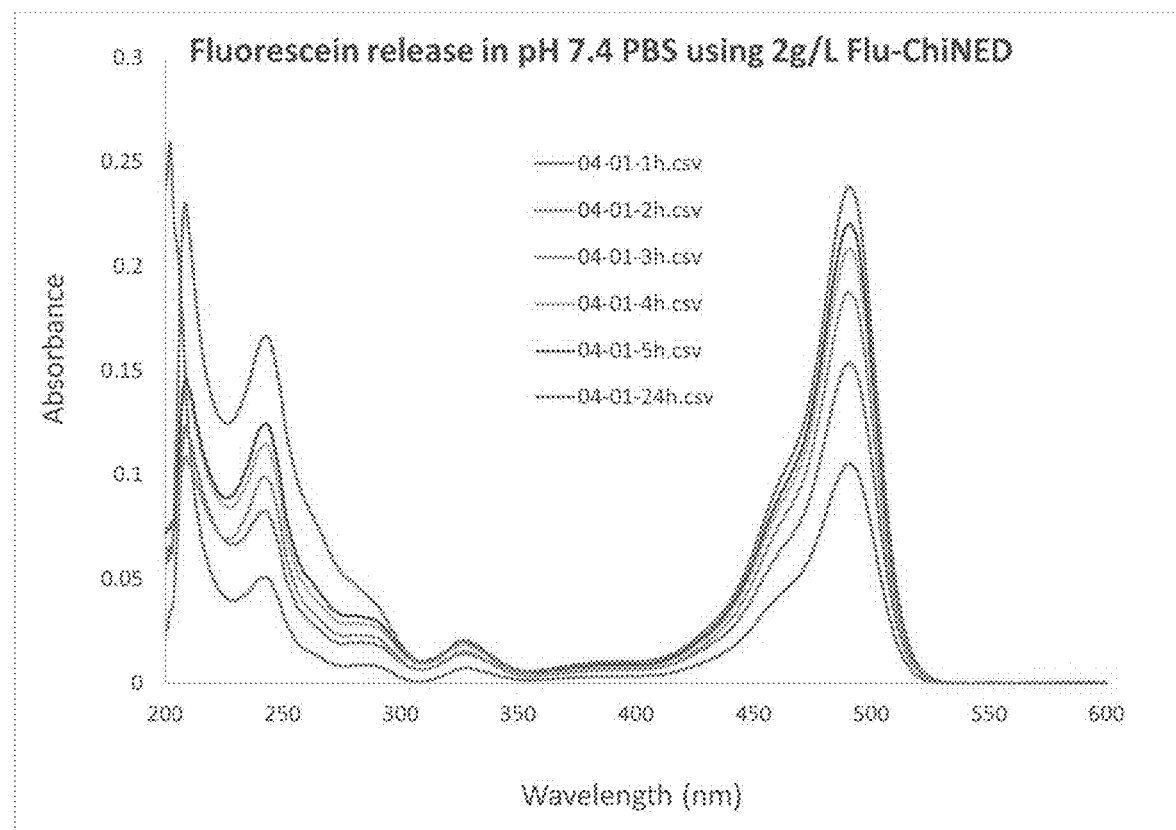
FIG. 8 are UV-Vis spectra of fluorescein release from the fluorescein-nanocomposite conjugate in pH 7.4 phosphate buffer medium after 1, 2, 3, 4, 5, and 24 hours (bottom to top curves respectively).

Fluorescein release from the fluorescein-nanocomposite conjugate (2 g/L) was investigated in pH 7.4 phosphate buffer medium. UV-Vis spectrum of the buffer was analyzed at different time intervals to determine the amount of released drug at the 490 nm peak. FIG. 8, and Table 1, below, show the drug release profile obtained in ambient conditions. In FIG. 8, fluorescein release is shown to increase over time from 1 hour to 24 hours (bottom spectrum to top spectrum).

TABLE 1

Fluorescein release from polymer-coated nanocomposites in PBS over time

| Time (h) | Fluorescence release (mM) | Fluorescence release (μg) |
|---|---|---|
| 1 | 0.001485 | 49.348035 |
| 2 | 0.002166 | 71.978346 |
| 3 | 0.00264 | 87.72984 |
| 4 | 0.00293 | 97.36683 |
| 5 | 0.00309 | 102.68379 |
| 24 | 0.00335 | 111.32385 |

Example 8: Preparation of $CuO_{(1-x)}ZnO_x$ Nanocomposite Coated with Chitosan-Ibuprofen Conjugate Ibuprofen is a nonsteroidal anti-inflammatory drug (NSAID) used to treat pain, fever, and inflammation. Ibuprofen loading into and release from the described polymer-coated nanocomposite is described in the following steps.

Step 1. In the first step, a water-soluble modified chitosan was prepared. The simplest modification is through synthesis of chitosan mesylate salt or chitosan chloride. Chitosan (1 g) was suspended in water (80 ml) at ~10° C. To this, methane sulfonic acid or HCl (~1 mL) was added dropwise until the solution became clear. The solution was stirred for an additional hour. Resulting modified chitosan was purified by 48 h dialysis against deionized water.

Step 2. In the second step, ibuprofen-chitosan conjugate was prepared. Ibuprofen (5 mg) was dissolved under basic condition (7 drops of 0.1M NaOH in 5 mL of DIW) and stirred for 3 h. Water soluble chitosan Chi-HCl (50 mg), prepared as in Step 1, was diluted in water (20 mL). Ibuprofen solution was added dropwise to Chi-HCl and stirred for 30 min.

Step 3. In the third step, ibuprofen-chitosan conjugate was coated over the nanocomposite. $CuO_{(1-x)}ZnO_x$ nanocomposite (0.5 g) was suspended in DIW (50 mL) under ultrasonication (90%-amplitude, 5 min). To the nanocomposite suspension, ibuprofen-chitosan conjugate solution was added dropwise and stirred overnight. The suspension was centrifuged twice at 10,000 rpm for 5 min.

Ibuprofen loading efficiency was determined from the UV-Vis spectrum of supernatant according to the equation, measuring absorbance at 221 nm: Drug loading efficiency (%)=(Amount of drug loaded/Total amount of drug used)×100.

Drug loading efficiency was 49.7% when done according to the described method (drug loaded onto polymer and then nanocomposite coated with drug-polymer conjugate). It was observed that the ibuprofen loading sequence was critical for achieving higher loading efficiency. When ibuprofen was added to preformed chitosan coated nanocomposite, the loading efficiency was only 8.0%.

Figure 9:
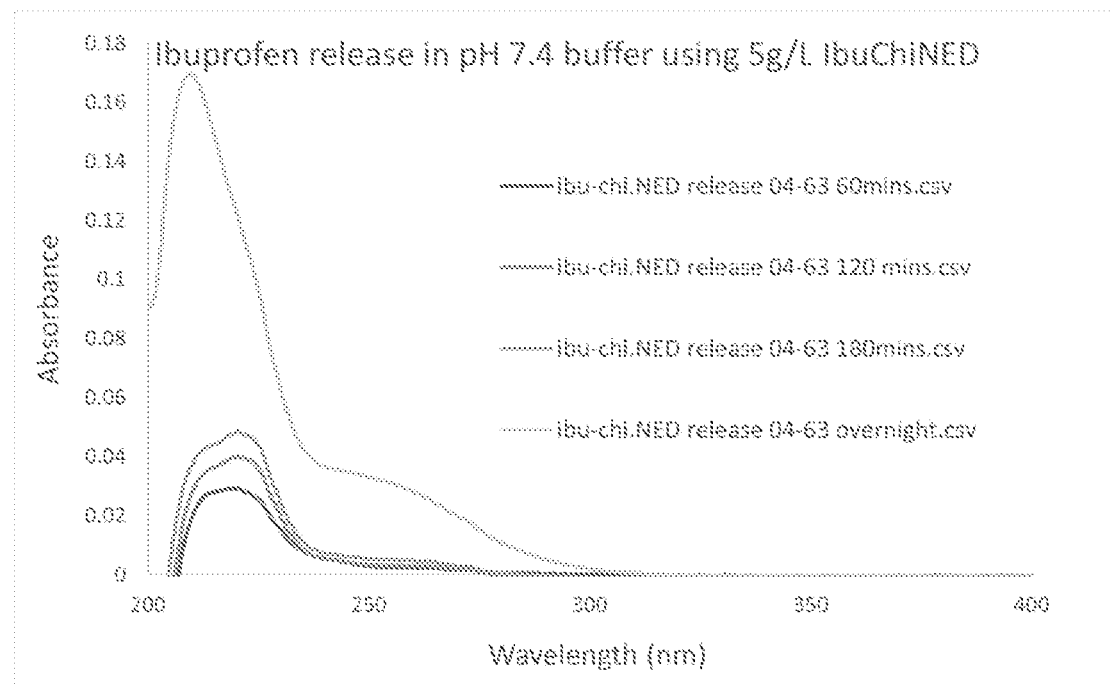
FIG. 9 are UV-Vis spectra of ibuprofen release from the ibuprofen-nanocomposite conjugate in pH 7.4 phosphate buffer medium after 60 minutes, 90 minutes, 180 minutes, and overnight (bottom to top curves respectively).

Ibuprofen release from the ibuprofen-nanocomposite conjugate (5 g/L) was investigated in pH 7.4 phosphate buffer medium. UV-Vis spectrum of the buffer was analyzed at different time intervals to determine the amount of released drug, observed at the 221 nm absorbance peak. Absorbance spectra at 60 minutes, 120 minutes, 180 minutes, and overnight are shown in FIG. 9. Drug release profile obtained in ambient conditions is also shown below in Table 2. As with the fluorescein release observed in Example 1, after an initial larger amount at the first time point measured, ibuprofen release increases gradually over time.

TABLE 2

Ibuprofen release from polymer-coated nanocomposites in PBS over time

| Time (min) | Concentration (μM) |
|---|---|
| 60 | 2.89 |
| 120 | 4.0 |
| 180 | 4.9 |
| 1440 | 11.8 |

Example 9: Preparation of $CuO_{(1-x)}ZnO_x$ Nanocomposite Coated with Alginate-Tetracaine Conjugate Tetracaine is a local anesthetic drug commonly used for topical application. Tetracaine loading into and release from the described polymer-coated nanocomposite is described in the following steps.

Step 1. In this step, tetracaine-alginic acid conjugate was prepared. Alginic acid sodium salt (50 mg) was dissolved in DIW. Tetracaine hydrochloride (5 mg) was added and the solution was stirred for 4 h.

Step 2. In the second step, tetracaine-alginic acid conjugate was coated over the nanocomposite. $CuO_{(1-x)}ZnO_x$ (0.5 g) nanocomposite was suspended in DIW (50 mL) under ultrasonication (90%-amp, 4 min). To the nanocomposite suspension, the above tetracaine-alginate conjugate solution was added dropwise. pH of the reaction was adjusted to 7, 8, or 9, and the suspension stirred overnight. The suspension was centrifuged at 10,000 rpm for 5 min to collect coated nanocomposite.

Tetracaine loading efficiency was determined from the UV-Vis spectrum of supernatant, which presents a peak at 315 nm, using the formula: Drug loading efficiency (%)= (Amount of drug loaded/Total amount of drug used)×100.

Drug loading efficiency was observed to be pH dependent, and was 51% for the reaction performed at pH 7, 65.5% for the reaction performed at pH 8, and 77.9% for the reaction performed at pH 9.

Figure 10:
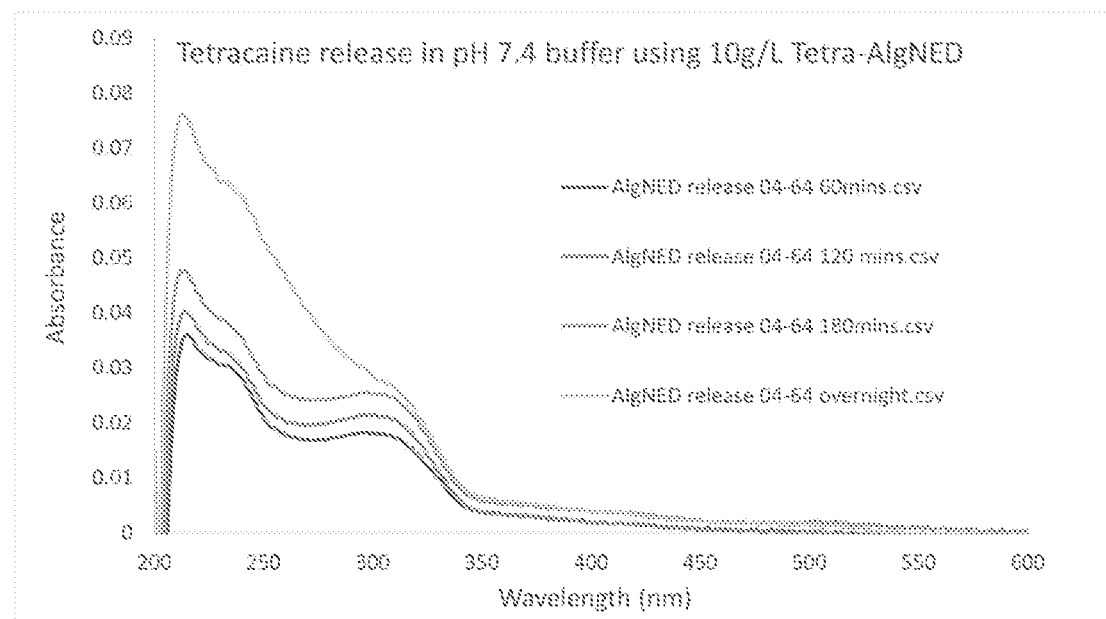
FIG. 10 are UV-Vis spectra of tetracaine release from the ibuprofen-nanocomposite conjugate in pH 7.4 phosphate buffer medium after 60 minutes, 90 minutes, 180 minutes, and overnight (bottom to top curves respectively).

Tetracaine release from the tetracaine-nanocomposite conjugate (5 g/L) was investigated in pH 7.4 phosphate buffer medium. UV-Vis spectrum of the buffer was analyzed at different time intervals to determine the amount of released drug, observed at the 315 nm absorbance peak. Absorbance spectra at 60 minutes, 120 minutes, 180 minutes, and overnight are shown in FIG. 10. Drug release profile obtained in ambient conditions is also shown below in Table 3. As with the fluorescein release observed in Example 1, after an initial larger amount at the first time point measured, tetracaine release increases gradually over time.

TABLE 3

Tetracaine release from polymer-coated nanocomposites in PBS over time

| Time (min) | Concentration (μM) |
|---|---|
| 60 | 0.77 |
| 120 | 0.915 |
| 180 | 1.09 |
| 1440 | 1.17 |

Example 10: Preparation of $CuO_{(1-x)}ZnO_x$ Nanocomposite Coated with Alginate-Procaine Conjugate Procaine is local anesthetic drug of the amino ester group. Procaine loading into and release from the described polymer-coated nanocomposite is described in the following steps.

Step 1. In this step, procaine-alginic acid conjugate was prepared. Alginic acid sodium salt (50 mg) was dissolved in DIW. Procaine hydrochloride (5 mg) was added and the solution stirred for 4 h.

Step 2. In the second step, procaine-alginic acid conjugate was coated over the nanocomposite. $CuO_{(1-x)}ZnO_x$ (0.5 g) nanocomposite was suspended in DIW (50 mL) under ultrasonication (90%-amp, 4 min). To the nanocomposite suspension, the procaine-alginate conjugate solution was added dropwise. pH of the reaction was adjusted to 9 or left unchanged, and the suspension was stirred overnight. The suspension was centrifuged at 10,000 rpm for 5 min to collect coated nanocomposite. Procaine loading efficiency was determined from the UV-Vis spectrum of supernatant (with the procaine absorbance peak being 290 nm) using the formula: Drug loading efficiency (%)=(Amount of drug loaded/Total amount of drug used)×100.

Examination of absorbance spectra of supernatant demonstrated that drug loading efficiency was 40.4% for the reaction without pH adjustment and 43.8% for the reaction performed at pH 9.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A metal oxide semiconductor nanocomposite composition, comprising:
   a metal oxide nanomaterial consisting of a CuO and ZnO nanomaterial consisting of clusters of CuO and ZnO quantum dots, wherein the nanomaterial has a chemical formula of $CuO_{(1-x)}ZnO_x$, wherein X is the atomic ratio of zinc oxide impurities in the nanomaterial;
   a hemostasis-promoting polymer coating the metal oxide nanomaterial, comprising chitosan and derivatives thereof, calcium salt of alginate and divalent cation alginate derivatives thereof, polylysine, or oxidized cellulose; and
   a pharmaceutically active drug conjugated to the hemostasis-promoting polymer.

2. The metal oxide semiconductor nanocomposite composition of claim 1, wherein the metal oxide nanomaterial consists of a surface region and a core region, wherein the surface region comprises greater than 25% ZnO by weight and less than 75% CuO by weight, and wherein the core region comprises less than 10% ZnO by weight and greater than 90% CuO by weight.

3. The metal oxide semiconductor nanocomposite composition of claim 1, wherein the hemostasis-promoting polymer is from 1% to about 10% of the metal oxide semiconductor nanocomposite by weight.

4. The metal oxide semiconductor nanocomposite composition of claim 1, wherein the thickness of the hemostasis-promoting polymer coating is from about 1.0 nm to about 10.0 nm.

5. The metal oxide semiconductor nanocomposite composition of claim 1, wherein the hemostasis-promoting polymer is selected from the group consisting of chitosan, alginate, gelatin, carboxymethyl cellulose, and polyethylene glycol.

6. The metal oxide semiconductor nanocomposite composition of claim 1, wherein the pharmaceutically active drug conjugated to the hemostasis-promoting polymer is a small molecule compound or biological molecule.

7. The metal oxide semiconductor nanocomposite composition of claim 1, wherein the pharmaceutically-active drug is selected from the group consisting of an analgesic, opioid, local anesthetic, and non-steroidal anti-inflammatory drug (NSAID).

8. The metal oxide semiconductor nanocomposite composition of claim 1, wherein the pharmaceutically-active drug is an analgesic and/or anti-inflammatory drug selected from the group consisting of tetracaine, tetracaine hydrochloride, procaine, procaine hydrochloride, ibuprofen, lidocaine, diclofenac, acetaminophen, and aspirin.

9. The metal oxide semiconductor nanocomposite composition of claim 1, wherein the pharmaceutically-active drug is conjugated to the polymer by covalent or non-covalent interactions.

10. A pharmaceutical composition comprising the metal oxide semiconductor nanocomposite composition of claim 1 and a pharmaceutically acceptable salt, carrier, or excipient.

11. A method for treating a wound comprising, contacting a wound with the pharmaceutical composition of claim 10, wherein the drug is released to the site of contact.

12. The method of claim 11, wherein the drug is gradually released as a burst or over an extended period in response to changes in local pH, temperature changes, hydrolysis, an enzyme-catalyzed release, or combinations thereof.

13. The method of claim 11, wherein the composition is antimicrobial, hemostatic, anesthetic, anti-inflammatory, or a combination thereof.

14. The method of claim 11, wherein the composition is formulated for administration by first-aid gauze, wound dressing foams and films, topical ointment, or topical spray.

15. A method for inhibiting microbial growth in a subject comprising, administering to a subject in need thereof the metal oxide semiconductor nanocomposite composition of claim 1, wherein the microbe is bacteria, fungi, or virus.

16. The method of claim 15, wherein the metal oxide semiconductor nanocomposite composition is formulated for topical administration by first-aid gauze, wound dressing foams and films, topical ointment, or topical spray.

17. A method for producing a metal oxide semiconductor nanocomposite composition, comprising:
   providing a metal oxide nanocomposite composition;
   solubilizing a polymer selected from the group consisting of chitosan, alginate, gelatin, carboxymethyl cellulose, and polyethylene glycol;
   conjugating a pharmaceutical drug to the polymer, thereby producing a polymer-drug conjugate; and
   coating the metal oxide nanocomposite composition with the polymer-drug conjugate, wherein drug loading efficiency to the polymer-drug conjugate is from 10% to about 90%.

* * * * *